(12) United States Patent
Stevens et al.

(10) Patent No.: US 9,233,885 B2
(45) Date of Patent: Jan. 12, 2016

(54) TWO STAGE OXYGENATE CONVERSION REACTOR WITH IMPROVED SELECTIVITY

(75) Inventors: Carl J. Stevens, Lake Forest, IL (US); Paul A. Sechrist, South Barrington, IL (US); Richard A. Johnson, II, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 325 days.

(21) Appl. No.: 12/793,290

(22) Filed: Jun. 3, 2010

(65) Prior Publication Data
US 2011/0301393 A1    Dec. 8, 2011

(51) Int. Cl.
C07C 1/20    (2006.01)
B01J 8/26    (2006.01)

(52) U.S. Cl.
CPC ... *C07C 1/20* (2013.01); *B01J 8/26* (2013.01); *B01J 2208/00212* (2013.01); *B01J 2219/0004* (2013.01); *C07C 2529/85* (2013.01)

(58) Field of Classification Search
CPC .......................................................... C07C 1/24
USPC ......... 585/463, 638, 639, 640, 809, 833, 641, 585/642
See application file for complete search history.

(56) References Cited

U.S. PATENT DOCUMENTS

| | | | |
|---|---|---|---|
| 3,978,150 A | 8/1976 | McWilliams, Jr. | |
| 5,026,935 A | 6/1991 | Leyshon et al. | |
| 5,026,936 A | 6/1991 | Leyshon et al. | |
| 5,914,433 A | 6/1999 | Marker | |
| 6,166,282 A | 12/2000 | Miller | |
| 6,858,133 B2 | 2/2005 | Dath et al. | |
| 6,867,341 B1 | 3/2005 | Abrevaya et al. | |
| 7,087,155 B1 | 8/2006 | Dath et al. | |
| 7,132,580 B1 * | 11/2006 | Senetar | 585/639 |
| 7,268,265 B1 | 9/2007 | Stewart et al. | |
| 7,375,257 B2 | 5/2008 | Dath et al. | |
| 7,568,018 B1 | 7/2009 | Hove et al. | |
| 2004/0064007 A1 * | 4/2004 | Beech et al. | 585/639 |
| 2006/0025646 A1 * | 2/2006 | Fung et al. | 585/639 |
| 2006/0135834 A1 * | 6/2006 | Xu et al. | 585/639 |

OTHER PUBLICATIONS

U.S. Appl. No. 12/793,276, filed Jun. 3, 2010, Stevens et al.

\* cited by examiner

*Primary Examiner* — In Suk Bullock
*Assistant Examiner* — Sharon Pregler

(57) ABSTRACT

A process and apparatus is presented for the improved selectivity of oxygenate conversion to olefins. The process includes passing a process stream through a two stage reactor, wherein the process stream is separated from the catalyst in the first stage before passing the process stream to the second stage. The catalyst is continuously passed through the two stages, and cycles through a regeneration unit to control the carbon content on the catalyst.

15 Claims, 1 Drawing Sheet

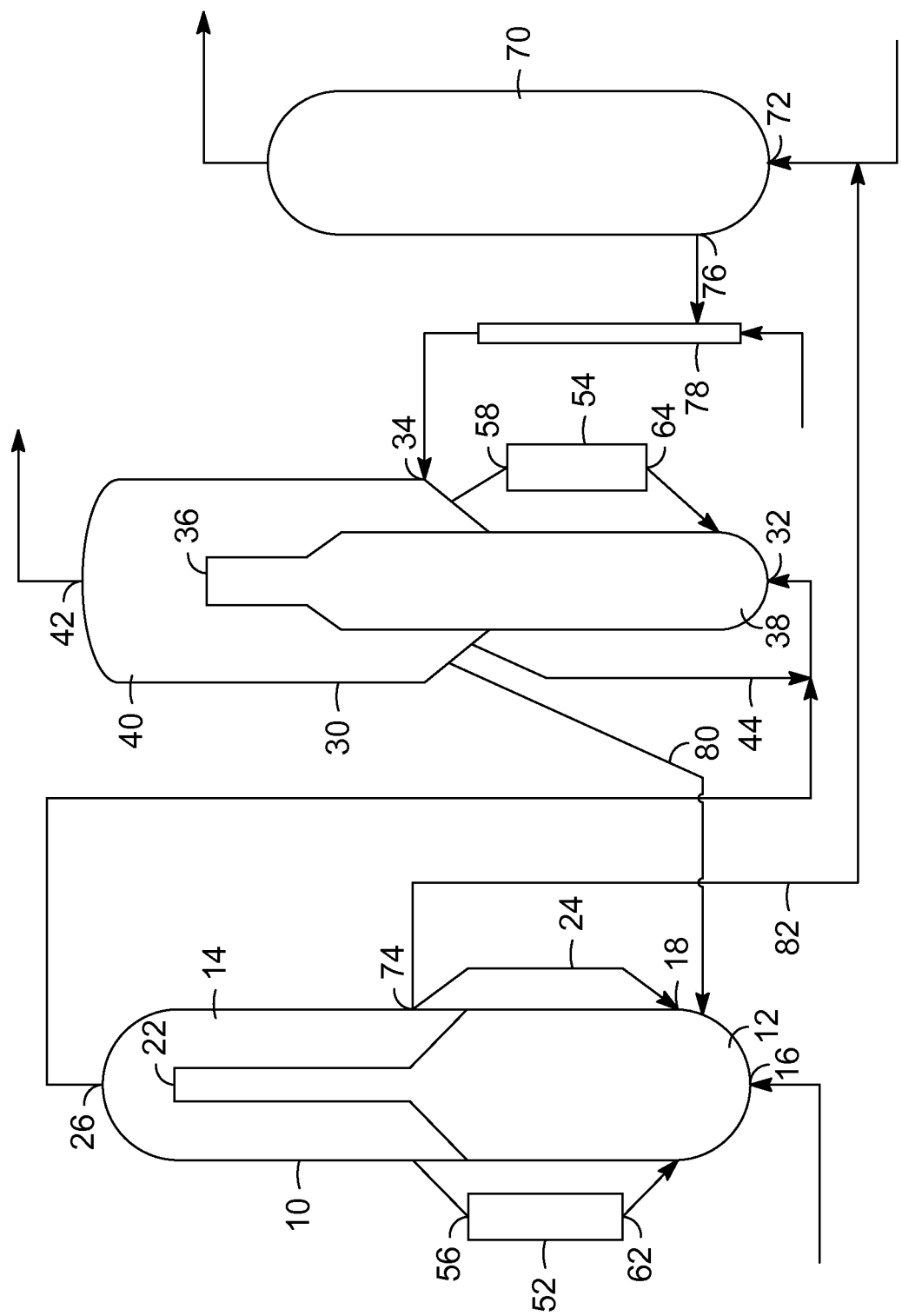

TWO STAGE OXYGENATE CONVERSION REACTOR WITH IMPROVED SELECTIVITY

FIELD OF THE INVENTION

The field of the invention is the process for conversion of methanol to olefins. In particular, the methanol to olefins process uses a new reactor design for increasing the selectivity of methanol to olefins.

BACKGROUND OF THE INVENTION

The traditional method of olefin production is the cracking of petroleum feedstocks to olefins. The cracking of petroleum feedstocks is done through catalytic cracking, steam cracking, or some combination of the two processes. The olefins produced are generally light olefins, such as ethylene and propylene. There is a large market for the light olefin products of ethylene and propylene. As petroleum feedstocks from crude oil face increasing prices it is advantageous to provide for other sources of ethylene and propylene.

An ethylene plant involves a very complex combination of reaction and gas recovery systems. Feedstock is charged to a thermal cracking zone in the presence of steam at effective conditions to produce a pyrolysis reactor effluent gas mixture. The mixture is then stabilized and separated into purified components through a sequence of cryogenic and conventional fractionation steps. Ethylene and propylene yields from steam cracking and other processes may be improved using known methods for the metathesis or disproportionation of $C_4$ and heavier olefins, in combination with a cracking step in the presence of a zeolitic catalyst, as described, for example, in U.S. Pat. No. 5,026,935 and U.S. Pat. No. 5,026,936. The cracking of olefins in hydrocarbon feedstocks comprising $C_4$ mixtures from refineries and steam cracking units is described in U.S. Pat. No. 6,858,133; U.S. Pat. No. 7,087,155; and U.S. Pat. No. 7,375,257.

Paraffin dehydrogenation represents an alternative route to light olefins and is described in U.S. Pat. No. 3,978,150 and elsewhere. More recently, the desire for alternative, non-petroleum based feeds for light olefin production has led to the use of oxygenates such as alcohols and, more particularly, methanol, ethanol, and higher alcohols or their derivatives. The alcohols, and in particular methanol, can be produced from other sources such as biomass and natural gas. The most common conversion of oxygenates to olefins is the production of light olefins from methanol, and one process is described in U.S. Pat. No. 5,914,433. The yield of light olefins from such a process may be improved using olefin cracking to convert some or all of the $C_4^+$ product of MTO in an olefin cracking reactor, as described in U.S. Pat. No. 7,268,265. Other processes for the generation of light olefins involve high severity catalytic cracking of naphtha and other hydrocarbon fractions. A catalytic naphtha cracking process of commercial importance is described in U.S. Pat. No. 6,867,341.

The process of converting oxygenates to olefins is an important process for utilizing oxygenates, such as methanol, and converting them to higher value products such as monomers for plastics, such as ethylene and propylene. The process of converting oxygenates to olefins is a catalytic process, and the catalyst is usually a molecular sieve catalyst. Among the molecular sieves that are useful for the catalytic process are ZSM-type molecular sieves, but more particularly, it has been found that silico-aluminophosphate (SAPO) molecular sieves work well in the process.

Even with the different methods of producing light olefins, the demand for ethylene and propylene continues to increase. Therefore, a need exists for new methods, catalysts and equipment that can increase light olefin yields from existing sources of both straight-run and processed hydrocarbon streams.

SUMMARY OF THE INVENTION

The process of the present invention comprises a controlling the flow of catalyst and process stream through a two stage fast-fluidized bed reactor for carrying out an oxygenate conversion reaction with a significantly reduced catalyst inventory compared to traditional bubbling bed reactors. By using a two stage reactor system with the catalyst continuously flowing through the apparatus, the size of the regenerator can be reduced, and an improved selectivity is attained.

The process for the conversion of oxygenates to olefins comprises passing an oxygenate feedstream to a first stage reactor, wherein the reactor comprises a fluidized bed. The oxygenate is contacted with a catalyst in the fluidized reactor bed thereby creating an intermediate stream, comprising the catalyst and an fluid stream having partially converted oxygenate to olefins. The catalyst is separated from the intermediate stream, wherein at least 96% of the catalyst is removed from the intermediate stream, resulting in a first returned catalyst stream and an intermediate product stream comprising olefins. The first returned catalyst stream is returned to the first stage reactor, and the intermediate product stream is passed to a second stage reactor. The intermediate product stream is contacted with a catalyst in fluidized bed in the second stage reactor, thereby creating an effluent stream. The effluent stream comprises catalyst and product, and is separated into a second returned catalyst stream and a product stream comprising olefins. The second returned catalyst stream is passed back to the second stage reactor.

In one embodiment, the returned catalyst in the first returned catalyst stream and the second returned catalyst stream is cooled. This provides thermal control of the reactor to prevent unwanted thermal cracking of the olefins generated in the process.

In another embodiment, the process comprises passing a portion of the first returned catalyst stream to a regeneration unit. The regeneration unit regenerates the catalyst by burning off the carbon deposits on the catalyst produced during the dehydrogenation reaction. The portion of the first returned catalyst stream passed to the regeneration unit is less than 50% of the total first returned catalyst stream. The regeneration unit produces a regenerated catalyst stream, which is passed to the catalyst inlet of the second stage reactor unit. Catalyst in the second stage reactor unit is cycled through the reactor bed, and a portion of the second returned catalyst stream is passed to the first stage reactor. By controlling the separation of the catalyst from the process streams and cycling of the catalyst through the reactors, it has been determined that the regeneration unit can be reduced in size by as much as 40%, thereby providing significant savings in equipment and operation costs.

Additional objects, embodiments and details of this invention can be obtained from the following drawing and detailed description of the invention.

BRIEF DESCRIPTION OF THE DRAWING

The FIGURE is a diagram of the apparatus and process for the present invention.

DETAILED DESCRIPTION OF THE INVENTION

The production of an olefin product stream is dependent on the reactor and the reaction kinetics, the hydrodynamics, and the deactivation of the catalyst. A new design for an oxygenate to olefins reactor system is presented. The design comprises a two reactor system wherein the reactants flow through both reactors, and the reactors have fluidized beds where the catalyst is recirculated through each reactor. The system includes passing the catalyst back through the two reactor stages, and cycles the catalyst through a regeneration unit. The control of the process and rate of recycle allows for a much smaller regeneration unit.

The system is best illustrated by the FIGURE. The reactor system comprises a two stage reactor, with a first stage reactor 10 made up of a fluidized bed reactor 12 and a separation unit 14. The first stage reactor 10 has a fluid inlet 16, a catalyst inlet 18 and a catalyst and fluid outlet 22. The catalyst and fluid leaving the catalyst and fluid outlet 22 of the first stage reactor 12 are passed to the separation unit 14, where the catalyst and fluid are separated, and the catalyst is returned to the first stage reactor 12 through a first catalyst recirculation channel 24, and the fluid is passed out as an intermediate product stream through the first separation unit fluid outlet 26. The reactor system further includes a second stage reactor 30 having a fluid inlet 32 in fluid communication with the intermediate product stream outlet 26. The second stage reactor further includes a catalyst inlet 34 and a catalyst and fluid outlet 36. The second stage reactor includes a second fluidized bed reactor 38 and a second separation unit 40 wherein the catalyst and fluid from the reactor 38 are separated thereby created a product stream passing through a product stream outlet 42, and passing the catalyst out a second catalyst outlet and returned to the reactor 38 through a second catalyst recirculation channel 44.

The reactor system can further include catalyst coolers for each stage of the reactor system. The first stage reactor 10 includes a cooler 52 to allow control of the temperature of the first stage reactor 10 by controlling the temperature of the catalyst, and the second stage reactor 30 has a cooler 54 to allow control of the temperature of the second stage reactor 30 by controlling the temperature of the catalyst. Each cooler 52, 54 has an inlet 56, 58 in fluid communication with the respective reactor bed catalyst outlets, and an outlet 62, 64 in fluid communication with the respective reactor bed catalyst inlets.

The catalyst is recirculated continuously, and when leaving the reactor beds 12, 38, the catalyst is separated from the product stream and recycled. The reactor system separation units 14, 40 recover at least 96% of the catalyst carried out of the catalyst and fluid outlets 22, 36. Preferably the separation of catalyst from the product stream is at least 98% of the catalyst, and more preferably at least 99% of the catalyst is removed from the product stream before passing the intermediate product stream or the product stream out of the first and second stage reactors 10, 30.

In one embodiment, the reactor system includes a regeneration unit 70. The regeneration unit 70 has a catalyst inlet 72 in fluid communication with the first stage reactor catalyst outlet 74. The regeneration unit 70 further includes a catalyst outlet 76 in fluid communication with the second stage reactor 40 catalyst inlet 34. The catalyst can be transported from the regenerator 70 to the second stage reactor 40 through a catalyst lift riser 78. The reactor system includes a catalyst transfer line 80 from the second separation unit 40 to a first reactor bed 12 catalyst inlet. The inlet can be a separate inlet, or can be the same inlet as the first catalyst inlet 18. The first separation unit 14 includes an outlet, with a conduit 82 for passing a portion of the catalyst separated from the first catalyst bed effluent stream to the regeneration unit 70.

The reactor system sets up a partially counter-current flow of catalyst and reactants, where the reactants flow from through the first stage reactor, and then through the second stage reactor. The catalyst is regenerated and passed from the regenerator to the second stage reactor and then passed to the first stage reactor. The process of the present invention provides for the conversion of oxygenates to olefins, and uses a regenerator that can be reduced in size by up to 40%, based on the catalyst space-time.

The process comprises passing an oxygenate feedstream to the first stage reactor 12. The feedstream is contacted with a catalyst in a fluidized bed in the first stage reactor creating an intermediate stream. Catalyst is separated from the intermediate stream, recovering at least 96% of the catalyst for return to the first stage reactor. The separated intermediate stream, comprising olefins, is passed to the second stage reactor. In the second stage reactor the intermediate product stream is contacted with a catalyst in a fluidized bed, thereby creating an effluent stream. The catalyst is separated from the effluent stream, recovering at least 96% of the catalyst and returned to the second stage reactor. A product stream is produced comprising olefins.

The feedstream to the reactor is preferably preheated to a temperature in the range between 120° C. and about 210° C. A preferred preheated feedstream temperature is in the range of 180° C. and 210° C., with the feedstream temperature held below or at 210° C. to minimize thermal decomposition of the feedstream.

Each reactor stage is operated at a temperature in the range from 200° C. to 700° C., with a preferred temperature range of 300° C. to 600° C., and a more preferred temperature range of 400° C. to 550° C. The reaction conditions of each reactor stage includes a pressure in the range of 0.1 kPa to 10 MPa, with a preferred pressure in the range of 100 kPa to 800 kPa, and more preferably in the range 170 kPa to 800 kPa.

The choice of operating pressure is also balanced with the ability to flow the reactants through the two stage reactor system without additional intermediate, or downstream compressors. The feedstream is an oxygenate, and a preferred feedstream is methanol, or other alcohols. To obtain the desired operating pressures, the feedstream can be pumped as a liquid to a selected pressure range, and then preheated to a selected temperature range. The preheating of the feedstream can vaporize the feedstream such that the reactor is operated with gas phase reactants.

In each stage, the catalyst is circulated through the reactor bed, with the catalyst at least partially separated from the reactor bed effluent stream, and then returned to the reactor bed catalyst inlet.

The process can further include cooling the catalyst in either or both of the reactor stages. In each reactor stage, when the catalyst is cooled, the catalyst is passed through a cooling unit as the catalyst is circulated through the reactor. The catalyst can be drawn off from the top of the reactor bed, or preferably the catalyst is at least partially separated from the catalyst bed effluent stream and then passed to a catalyst cooing unit. The cooled catalyst is then fed to the reactor bed inlet.

The process comprises continuously regenerating the catalyst, and cycling the catalyst through the two reactor stage beds. The regenerated catalyst is passed from the regenerator 70 to a catalyst lift riser 78. The lift riser 78 passes the catalyst to the catalyst inlet to the second stage reactor 38. The catalyst in the regenerator is heated to a temperature sufficient to burn off the coke that is deposited on the catalyst during the oxygenate conversion. In a preferred embodiment, the catalyst is regenerated by burning off coke, or carbonaceous, deposits accumulated during the reactions. An oxidizing gas is passed to the regenerator 70 to oxidize the coke and regenerate the catalyst. The preferred oxidizing gas is air. Temperatures will typically be in the 500° C. to 700° C. range, and return a catalyst that can be too hot for use in the reactor. The catalyst can be passed to the upper stage of the second stage reactor 38, and subsequently be passed through the second stage catalyst cooler 54 to bring the catalyst temperature down to operating conditions for the second stage reactor 38.

In the second stage reactor 30, catalyst is carried out of the second reactor bed 38 and separated from the second reactor bed effluent stream. The catalyst is recycled for a second catalyst return stream to the second reactor bed 38. A portion of the returned catalyst is passed to the first reactor bed 12 in the first stage reactor 10. In one embodiment, the portion of catalyst from the second catalyst return stream that is passed to the first reactor bed 12 is less than 50% of the second catalyst return stream.

A portion of the catalyst separated from the second stage reactor bed effluent stream is passed to the inlet of the first stage reactor. As catalyst passes through the first fluidized reactor bed 12, a portion of the catalyst is carried out with the effluent from the first fluidized reactor bed 12, and returned to the catalyst bed. The effluent is separated in the first separation unit 14, and a portion of the catalyst separated from the effluent is passed to the regeneration unit 70.

The process includes a first catalyst return stream that is catalyst recovered from the first catalyst effluent stream and separated from the product stream. A portion of the catalyst from the first separation unit 14 to the regeneration unit 70 includes returning a portion that is less than 50% of the first catalyst return stream passed to the catalyst bed in the first stage reactor.

The new design shows the improved selectivity through simulations of the two stage reactor design over a base case of a one stage reactor design. The reactor and regenerator model has been developed that includes kinetics, hydrodynamics and long term catalyst deactivation. The model was used to determine the effects of multistage reactors on the conversion and selectivity.

Surprisingly, it has been determined that performance of each stage is dependent on the catalyst separation that is achieved in each stage of the reactor. In the first stage, it is preferable that more than 99% of the catalyst in the first stage reactor is separated from the intermediate product stream and recovered and recirculated to the first stage reactor. A small portion of the recirculated catalyst is passed to the regenerator for control of coke on the catalyst to a desired level.

The examples were performed with a combined reactor WHSV of 8, based on SAPO-34. The feed-rate to the first stage was 320,751 kg/hr, and the catalyst recirculation rate was the same within each reactor stage.

The results are presented in the following Tables, with the first Table showing the conditions of the catalyst flows and the second Table showing the hydrocarbon component distributions in the respective product streams.

TABLE 1

Examples of Conversion of Oxygenate through two stage reactors

| Example | Ex 1 | Ex 2a | Ex 2b | Ex 3a | Ex 3b | Ex 2 | Ex 3 | Ex 2 − Ex 1 | Ex 3 − Ex 1 |
|---|---|---|---|---|---|---|---|---|---|
| Conversion | 98 | 85.86 | 85.86 | 85.86 | 85.86 | 98 | 98 | 0 | 0 |
| SAPO conc, wt % | 30% | 30% | 30% | 30% | 30% | 30% | 30% | 0% | 0% |
| Rx temp | 480.92 | 476.14 | 484.44 | 479.21 | 481.05 | 477.17 | 479.44 | −3.75 | −1.48 |
| Wt. avg. coke (coke H/C = 0.6) on cat. | 1.19 | 2.42 | 1.40 | 2.08 | 1.68 | 2.29 | 2.03 | 1.10 | 0.83 |
| Coke (based on H/C = 0.6), kg/h | 5202 | 3661 | 634 | 3915 | 585 | 4296 | 4499 | −907 | −703 |
| Rx press, psig | 20.2 | 20.2 | 20.2 | 20.2 | 20.2 | 20.2 | 20.2 | 0.0 | 0.0 |
| Regen temp | 625 | 625 | 625 | 625 | 625 | 625 | 625 | 0 | 0 |
| Reactor WHSV | 8.00 | 9.34 | 55.85 | 14.40 | 18.00 | 8.00 | 8.00 | 0.00 | 0.00 |
| Recirculation | 0.98 | 0.92 | 1.76 | 0.98 | 0.98 | 1.03 | 0.98 | 0.05 | 0.00 |
| Catalyst Circ. (MT/hr) Single Stage | 484.3 | 168.2 | 50.5 | 209.5 | 38.7 | 191.6 | 217.5 | −292.7 | −266.8 |
| Coke after reaction | | | 0.6 | | 0.5 | | | | |
| Catalyst Flow-1st Stage to 2nd Stage | | | 149.8 | | 715.2 | | | | |
| Catalyst Circulation to Regenerator | 484.3 | 197.3 | | 240.7 | | 197.3 | 240.7 | −287.0 | −243.5 |
| Recirculation Total (MT/hr) | 32800 | 31569 | 33365 | 31099 | 32475 | 31792 | 31270 | −1008 | −1530 |
| 1st Stage Catalyst Separation Eff. | | 99.5% | | 97.7% | | | | | |
| Paraffins, etc | 8.0% | 6.6% | 7.9% | 7.0% | 7.3% | 6.8% | 7.1% | −1.2% | −0.9% |
| Circulation Cat/MeOH feed (dry basis) | 1.61 | 0.65 | | 0.80 | | 0.65 | 0.80 | −0.97 | −0.88 |
| ReCirculation Cat/Feed | 46.54 | 44.80 | 47.34 | 44.13 | 46.08 | 45.11 | 44.37 | −1.43 | −2.17 |
| kg cat/MT MeOH feed (dry basis) | 0.167 | 0.167 | 0.167 | 0.167 | 0.167 | 0.167 | 0.167 | 0 | 0 |
| Regenerator WHSV based on Feed | 0.49 | | | | | 0.82 | 0.73 | −0.97 | −0.88 |
| Reactor Diameter (ft) | 30.20 | 30.31 | 22.67 | 29.41 | 28.14 | | | | |

TABLE 2

| Example | Ex 1 | Ex 2a | Ex 2b | Ex 3a | Ex 3b | Ex 2 | Ex 3 | Ex 2 − Ex 1 | Ex 3 − Ex 1 |
|---|---|---|---|---|---|---|---|---|---|
| Selectivities | | | | | | | | | |
| Ethene | 35.61% | 37.24% | 35.91% | 36.79% | 36.42% | 37.07% | 36.74% | 1.46% | 1.13% |
| Propene | 35.61% | 37.24% | 35.91% | 36.79% | 36.42% | 37.07% | 36.74% | 1.46% | 1.13% |
| Butene | 11.92% | 12.06% | 12.10% | 12.09% | 12.09% | 12.07% | 12.09% | 0.15% | 0.17% |
| Pentene | 5.91% | 4.86% | 5.68% | 5.16% | 5.39% | 4.96% | 5.18% | −0.95% | −0.73% |
| Hexene | 2.96% | 1.98% | 2.54% | 2.16% | 2.33% | 2.05% | 2.18% | −0.91% | −0.78% |

TABLE 2-continued

| Example | Ex 1 | Ex 2a | Ex 2b | Ex 3a | Ex 3b | Ex 2 | Ex 3 | Ex 2 – Ex 1 | Ex 3 – Ex 1 |
|---|---|---|---|---|---|---|---|---|---|
| Methane | 1.02% | 1.02% | 1.08% | 1.03% | 1.04% | 1.02% | 1.03% | 0.01% | 0.01% |
| Ethane | 0.87% | 0.77% | 0.82% | 0.79% | 0.81% | 0.78% | 0.79% | −0.09% | −0.08% |
| Propane | 1.09% | 0.84% | 0.99% | 0.88% | 0.93% | 0.85% | 0.89% | −0.23% | −0.20% |
| CO | 0.03% | 0.03% | 0.03% | 0.03% | 0.03% | 0.03% | 0.03% | 0.00% | 0.00% |
| CO2 | 0.04% | 0.01% | 0.03% | 0.02% | 0.02% | 0.02% | 0.02% | −0.02% | −0.02% |
| Coke | 4.47% | 3.59% | 4.40% | 3.84% | 4.05% | 3.69% | 3.86% | −0.78% | −0.60% |
| Ethene + Propene | 71.22% | 74.47% | 71.81% | 73.58% | 72.84% | 74.14% | 73.49% | 2.92% | 2.27% |
| C4 + olefins | 20.8% | 18.9% | 20.3% | 19.4% | 19.8% | 19.1% | 19.5% | −1.7% | −1.3% |

The first example, Ex 1, is a single stage reactor, and is the base case for comparison with the new design. The model shows for the same overall space velocity, selectivity to light olefins was improved by operating a second stage riser reactor. In addition, the size of the regenerator can be reduced by more than 40% based on catalyst space time.

Example 2, Ex 2, is for the two stage reactor, and Ex 2a is for the performance of the first stage and Ex 2b is for the performance of the second stage. Example 3, Ex 3, Ex 3a and Ex 3b is similar to Ex 2, except for the separation of the catalyst in the first stage. The catalyst separation in the first stage for Ex 3a is 97.7%, while the catalyst separation for the first stage for Ex 2a is at 99.5%. The computed differences between the two cases having a two stage reactor system and the single stage reactor, Ex 1, are shown in the last two columns. The important differences show the increase in the amount of ethylene and propylene, along with a decrease in the amount of coke on the catalyst. It is evident that the two stage design yields significant improvement and savings. It is also evident, that the separation efficiency of the catalyst can affect the coke levels on the catalyst, and that the separation efficiency in turn affects the selectivity as well as the size of regenerator needed. A lower separation efficiency requires a larger regenerator. Changes in separation efficiency can also affect the space velocity of the catalyst, and the size of the second reactor. With lower first stage separation efficiency, the second stage reactor will need to be increased in diameter.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the conversion of oxygenates to olefins comprising:
    passing an oxygenate feedstream to a first stage reactor;
    contacting the oxygenate feedstream with a catalyst in a fluidized bed in the first stage reactor, thereby creating an intermediate stream;
    separating catalyst from the intermediate stream comprising olefins, wherein at least 96% of the catalyst is removed from the intermediate stream, thereby creating an intermediate product stream and a first returned catalyst stream, comprising a first portion and a second portion;
    returning the first portion of the first returned catalyst stream to the first stage reactor, wherein the first portion of the first returned catalyst stream comprises catalyst in the same form as recovered from the intermediate stream;
    passing the intermediate product stream to a second stage reactor;
    contacting the intermediate product stream with a catalyst in a fluidized bed in the second stage reactor, thereby creating an effluent stream;
    separating catalyst from the effluent stream thereby creating a product stream and a second returned catalyst stream;
    returning the second returned catalyst stream to the second stage reactor, wherein the second returned catalyst stream comprises catalyst in the same form as recovered from the effluent stream;
    passing the second portion of the first returned catalyst stream to a regenerator to create a regenerated catalyst stream; and
    passing the regenerated catalyst stream to the second reactor.

2. The process of claim 1 wherein the first stage reactor is operated at a temperature in the range of 200° C. to 700° C.

3. The process of claim 2 wherein the first stage reactor is operated at a temperature in the range of 400° C. to 550° C.

4. The process of claim 1 wherein the first stage reactor is operated at a pressure in the range of 0.1 kPa to 10 MPa.

5. The process of claim 4 wherein the first stage reactor is operated at a pressure in the range of 100 kPa to 800 kPa.

6. The process of claim 5 wherein the first stage reactor is operated at a pressure in the range of 170 kPa to 800 kPa.

7. The process of claim 1 wherein the oxygenate feed stream comprises methanol.

8. The process of claim 1 further comprising cooling the first returned catalyst stream.

9. The process of claim 1 further comprising cooling the second returned catalyst stream.

10. The process of claim 1 wherein the second stage reactor is operated at a temperature in the range of 200° C. to 700° C.

11. The process of claim 1 wherein the second stage reactor is operated at a pressure in the range of 0.1 kPa to 10 MPa.

12. The process of claim 1 wherein the second portion of the first returned catalyst stream is less than 50% of the first returned catalyst stream.

13. The process of claim 1 further comprising passing air to the regeneration unit.

14. The process of claim 1 further comprising passing the regenerated catalyst stream to the second stage reactor.

15. A process for the conversion of oxygenates to olefins comprising:
    passing an oxygenate feedstream to a first stage reactor;
    contacting the oxygenate feedstream with a catalyst in a fluidized bed in the first stage reactor, thereby creating an intermediate stream;
    separating catalyst from the intermediate stream comprising olefins, wherein at least 96% of the catalyst is removed from the intermediate stream, thereby creating an intermediate product stream and a first returned catalyst stream;

returning the first returned catalyst stream to the first stage reactor and passing the intermediate product stream to a second stage reactor;

passing a portion of the first returned catalyst stream to a regeneration unit;

passing the regenerated catalyst from the regeneration unit to the second stage reactor;

contacting the intermediate product stream with the regenerated catalyst in a fluidized bed in the second stage reactor, thereby creating an effluent stream;

separating catalyst from the effluent stream thereby creating a product stream and a second returned catalyst stream;

returning a portion of the second returned catalyst stream to the second stage reactor;

returning a portion of the second returned catalyst stream to the first stage reactor; and passing a regenerated catalyst stream to the second stage reactor.

* * * * *